United States Patent
Zurik

[11] Patent Number: 5,991,961
[45] Date of Patent: Nov. 30, 1999

[54] USER CUSTOMIZABLE BACK LOTION APPLICATOR, AND KIT RELATED THERETO

[76] Inventor: Rastislav Zurik, 5850 W. 87th St. 3B, Burbank, Ill. 60459

[21] Appl. No.: 09/123,511

[22] Filed: Jul. 28, 1998

[51] Int. Cl.⁶ ........................................... A47L 13/00
[52] U.S. Cl. ................... 15/210.1; 15/104.94; 15/209.1; 15/247
[58] Field of Search .............. 401/201; 15/104.94, 15/209.1, 235, 210.1, 244.1, 244.3, 247, 244.2; 206/229

[56] References Cited

U.S. PATENT DOCUMENTS

| | | | |
|---|---|---|---|
| 108,144 | 10/1870 | Hull | 401/266 |
| 1,431,881 | 10/1922 | Ericson-Smith | 15/104.94 |
| 2,315,054 | 3/1943 | Heber | 15/210.1 |
| 3,103,682 | 9/1963 | Markle . | |
| 3,430,282 | 3/1969 | Phillips | 15/244.1 |
| 3,876,314 | 4/1975 | Nehring . | |
| 3,891,331 | 6/1975 | Avery . | |
| 4,432,749 | 2/1984 | Snyder et al. . | |
| 4,658,461 | 4/1987 | Roe | 15/210.1 |
| 4,887,994 | 12/1989 | Bedford . | |
| 5,019,033 | 5/1991 | Geria . | |
| 5,358,480 | 10/1994 | Melcher et al. . | |
| 5,628,083 | 5/1997 | Hayes | 15/210.1 |
| 5,673,455 | 10/1997 | Per-Lee | 15/244.3 |
| 5,875,511 | 3/1999 | Nejdl | 15/244.1 |

*Primary Examiner*—Randall E Chin
*Attorney, Agent, or Firm*—Michael Best & Friedrich

[57] ABSTRACT

An ergonomically friendly back lotion applicator, method for making same, and kit for making same is provided herein. The ergonomically friendly back lotion applicator includes a substantially rigid handle sized and dimensioned to allow the user to access the back; and, an external applicator including a natural, porous, hide of an animal wrapped around a reslient material. The hide is capable of temporarily retaining and transferring the lotion, cream or oil from the hide to the back of the user, and is sized and dimensioned to automatically conform to at least a portion of the back upon application of pressure on the external applicator The external applicator removably connected to the handle. Optionally, the ergonomically friendly back lotion applicator is removably and magnetically mounted to the handle.

23 Claims, 3 Drawing Sheets

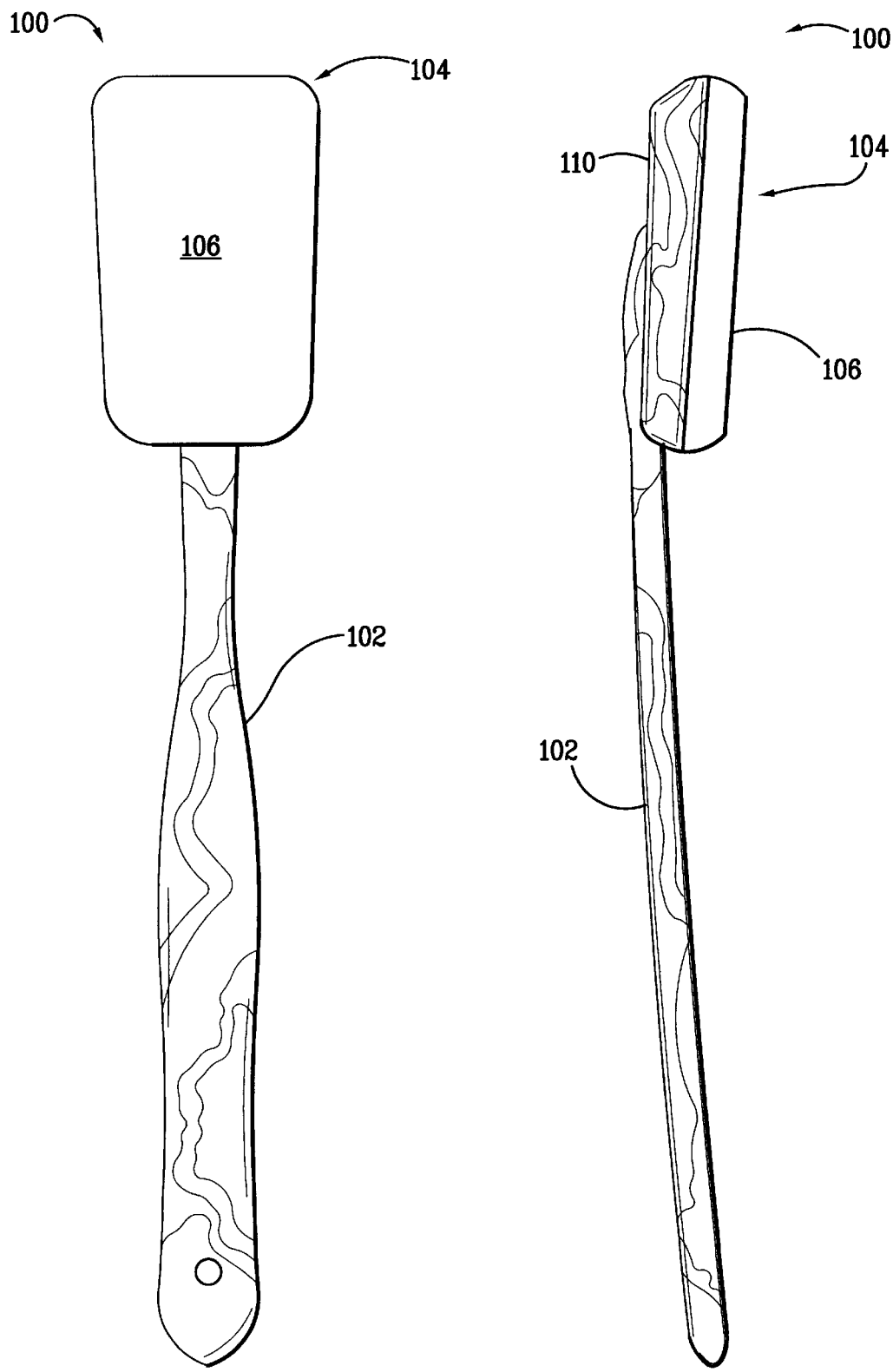

USER CUSTOMIZABLE BACK LOTION APPLICATOR, AND KIT RELATED THERETO

BACKGROUND OF THE INVENTION

This invention generally relates to lotion applicators; and, more particularly, it relates to a user customizable back lotion applicator for use in connection with the application of oils, creams and lotions to a user's back or other area of the body.

Various lotion applicators are known in the art. By way of example, these lotion applicators include those described in U.S. Pat. Nos. 5,736,213, 5,592,714, 5,240,339, 5,664,281, 5,341,538, 5,566,418, 4,906,118, 4,759,652, 5,360,111, 5,636,406, 4,964,744, 5,659,916, 4,396,028, 5,692,261, 5,573,342, 5,087,138, 5,035,523, 5,013,171, 4,896,984, 4,883,380, 3,699,980, D395,732, D395,099, D394,915, D394,108, D393,102, D392,411, D387,480, D385,060, D384,437, D381,765, D375,816, D375,382, D374,947, D370,085, D369,882, and D360,705.

The most serious drawback of these devices is that they are not field customizable. None of the devices described above allow the end user to customize the applicator in the field so that different applicators can be comfortably used at any desired location on the user's body.

It is an object of the present invention to solve the problems enumerated above.

SUMMARY OF THE INVENTION

The present invention provides an ergonomically friendly back lotion applicator for applying a lotion, cream or oil to a portion of a back of a user, and a kit for same. The lotion applicator includes a substantially rigid handle sized and dimensioned to allow the user to access the back. The handle is removably connected to an external applicator comprising a natural, porous, hide of an animal wrapped around a reslient material. The hide is capable of temporarily retaining and transferring the lotion, cream or oil from the hide to the back of the user, and is sized and dimensioned to automatically conform to at least a portion of the back upon application of pressure on the external applicator. In one embodiment, the natural, porous, hide of an animal is selected from the group consisting of a mammal hide, e.g. a deer hide, a cow hide, a lamb hide, and suede.

The objects and features of the present invention, other than those specifically set forth above, will become apparent in the detailed description of the invention and drawings set forth below.

BRIEF DESCRIPTION OF THE DRAWINGS

FIG. 1 is a top plan view of a lotion applicator of the present invention;

FIG. 2 is a side view of the external applicator of the lotion applicator of FIG. 1;

DETAILED DESCRIPTION OF THE INVENTION

Figure 3:
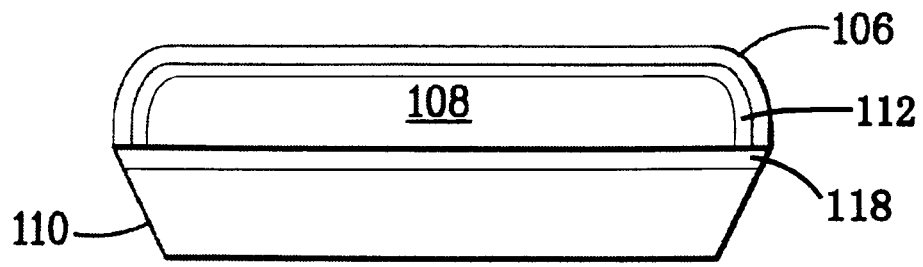
FIG. 3 is a front cross sectional view of a variant of the external applicator of FIG. 2.

FIG. 1 is a top plan view of ergonomically friendly back lotion applicator 100. Ergonomically friendly back lotion applicator 100 is used for applying a lotion, cream or oil to a portion of a back of a user. Lotions include skin care lotions, moisturizers, etc. Oils can include sun tan oils, baby oils, balms, etc. Various creams are also known in the art and include anti-aging creams, Vitamin A creams, etc.

Lotion applicator 100 includes a substantially rigid handle 102. Handle 102 is sized and dimensioned to allow the user to access his or her back, and is constructed of wood, plastic, rubber, metal, glass, etc. External applicator 104 is removably connected to the handle 102.

External applicator 104 includes a natural, porous, hide 106 of an animal wrapped around reslient material 108. External applicator 104 also optionally includes a back portion 110 made from rigid or substantially rigid material to support the rear of the applicator 104 and to provide to ease of connection to handle 102. Back portion 110 is constructed of a magnetically attracting material (material 118), a magnetically attracted material, or a combination thereof, so as to be matable with handle 102 and/or the remaining portion of external applicator 104.

Hide 106 is capable of temporarily retaining and transferring the lotion, cream or oil from the hide 106 to the back of the user. Hide 106 and the resilient material 108 is also sized and dimensioned to automatically conform to at least a portion of the back of the user upon application of pressure on external applicator 104 through handle 102. Hide 106 of an animal is selected from the group consisting of a mammal hide, and, by way or example, can include a deer hide, a cow hide, a lamb hide, and suede.

External applicator 104 includes a cream, lotion or oil barrier material 112 disposed between the hide 106 and the resilient material 108. The barrier material 112 prevents the resilient material 108 from absorbing the cream, lotion or oil. Exemplary barrier materials include plastics, wax papers, etc.

External applicator 104 is optionally sized and dimensioned to be substantially congruent to a musco-skeletal portion of the back. Applicator 104 can be molded to substantially conform to a lower back portion of a user, an upper back portion of a user, a lower neck portion of a user, a shoulder blade portion of a user, a vertebral portion of a user, etc.

Figure 4:
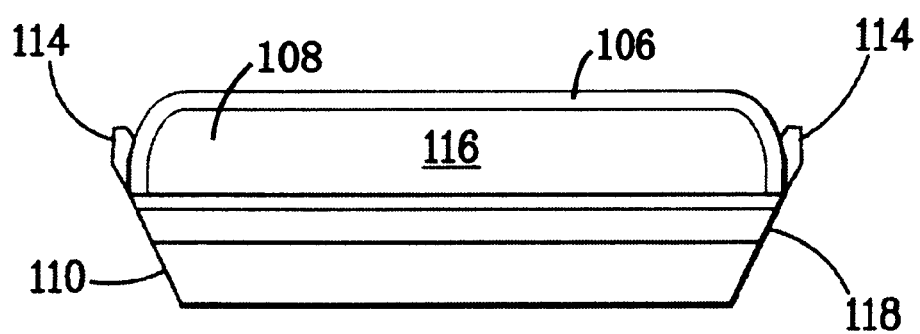
FIG. 4 is a front cross sectional view of a variant of the external applicator of FIG. 2; and, FIG. 5 is a front view of a kit of the present invention having several different external applicators.
Figure 5:
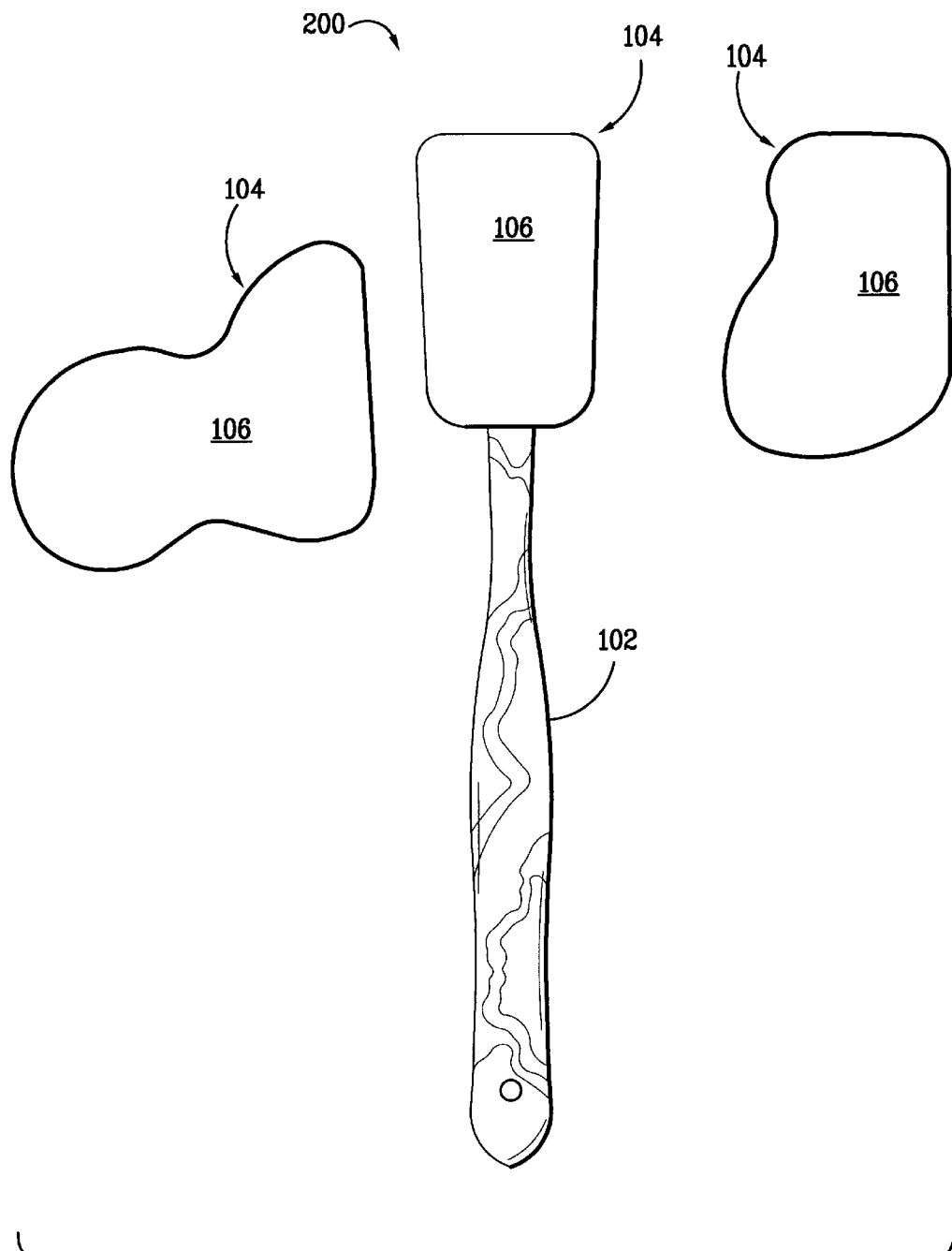

External applicator 104 also optionally includes side support 114. Side support 114 is also substantially rigid and can be constructed of the same material as back portion 110. The hide 106 and the resilient material 108 rise vertically above side support 114 as shown in FIG. 4.

In one variant of the invention, resilient material 108 is non-porous. In another variant of the invention, the resilient material 108 includes liquid filled bladder 116, a gel encapsulated in plastic, polymeric material sufficient to retain the gel, a curable composition, and/or a cured polyurethane.

The cured composition is generally a room temperature cured composition having a first part and a second part that are admixed prior to curing thereof to obtain final mix. A hardener is added to a base prepolymeric composition. The final mix generally includes a composition that can be selected from the group of urethane rubber, polyurethane, a casting resin, an epoxy, a silicone, a latex, a polysulfide compound, a silicone rubber, other elastomeric compositions, combinations thereof, and derivatives thereof. Optionally, a magnetically attracting material is added as a constituent of the final mix which is generally in liquid or gel form initially. Where the magnetic material is added to form a part of the external applicator 104 it is appreciated that external applicator is magnetically removable from handle 102, or back portion 110. Other optional constituents of the final mix, first part, and/or second part include a colored pigment, and/or catalyst.

Curable compositions are commercially available from Smooth-On, Inc., 1000 Valley Road, Gillette, N.J. 07933. These compositions include brand named compositions PMC-121/50, PMC-121/30, PMC-746, A 90 Liquid Rubber (U-10 urethane rubber liquids). PMC-121/50 consists of two liquid components, a Part A and a Part B. Part A includes a TDI prepolymer. Part A and Part B are mixed in a ratio of about 1:1 by weight or by volume. PMC-121/50 cures to an elastomer. These compositions are generally allowed to cure overnight (approximately 16 hours) at room temperature (25 degrees celsius). A cure accelerator can be optionally added to shorten the cure time.

PMC-746 includes a polyurethane compound. PMC-746 consists of two liquid components, a Part A and a Part B. Part A includes a TDI prepolymer. Part A and Part B are mixed in a ratio of about 2:1 by weight. PMC-121/50 cures to a strong durable rubber. Other polyurethane compounds include PL-25, PL-30, PL-35, PL-40. These PL-25-40 compounds are generally mixed one to one (Part A to Part B) by weight or by volume. PMC-724 is used in a mix of about 1 Part A to about 10 parts Part B by weight. Optionally Part D is added to thicken PMC-724 or part C is added to soften PMC-724. Other compounds used with the invention include PMC-744, BRUSH-ON 35, 50, A 60, A 70, PMC-770, and PMC-775 commercially available from Smooth-On, Inc.

Other curable compositions include urethane casting resins. These casting resins cure to hard plastics. Exemplary urethane casting resins include those commercially available from Smooth On, Inc.: Smooth-Cast 70-D, C-1504, C-1506, C-1508, C-1509, C-1511, C-1515, and Crystal Clear 200. These casting resins are generally mixed one to one (Part A to Part B) by volume. An optional filler can be added to these casting resins. Exemplary fillers include the brand names URE-FIL, or a glass spheres resin filler. Fillers are generally used to decrease the total cost/total mass of the device used herein.

Epoxy compounds, polysulfide compounds and liquid rubber compounds are also used herein as curable compositions. Epoxy compounds include epoxy casting compounds commercially available from Smooth-On, Inc. under the brand names A-3, A-30, C-1200, C-1210, and #20-136. Polysulfide compounds include FMC-100, FMC-200, FMC-201, FMC-205, and FMC-301. Liquid rubber compounds include brand named U-10-PL Series compounds, U-10-A60 series compounds, U-10 A70-X1 compounds, U-10-A90 series compounds, U-10 BP30 series compounds, U-10 BP30 series compounds, and U-10 -BP50 series compounds.

Silicone rubber compounds are also used as curable compositions with the present invention. Exemplary silicone rubber compounds include brand name GI-1000, GI-1032, GI-1100, GI-1120, GI-184, GI-320, GI-650, P-50, P-70, and P-90. A variety of additives can be added to the silicone rubber compounds described above including catalysts promoting the curing of the silicone rubber compounds as known in the art.

Part A and Part B are admixed to form final curable composition. The final curable composition is then poured into container or storage volume that provides the appropriate shape of external applicator 104. The liquid, pastelike, or gel-like composition is allowed to cure to obtain a cured composition. The cured composition is generally maelable and pliable.

The invention also includes a kit 200 for making a customized, ergonomically friendly back lotion applicator 100. The kit 200 includes at least one substantially rigid, handle 102 sized and dimensioned to allow the user to access the user's back, and a plurality of differently sized and dimensioned external applicators 104. The external applicators 104 having varying surface areas and surface contours as required to a particular area of a user's back. By way of example, surface contours can be such that they are concave or convex so as to be used on different portions of a user's back. The external applicator 104 is sized and dimensioned to be substantially congruent to a different musco-skeletal portion of the back. Hence, the user is capable of applying lotion to selected portions of the back.

The ergonomically friendly back lotion applicator also includes external applicator 104 that is optionally, removably, magnetically mounted to handle 102 by magnetically attracting material 118 (FIG. 3) that is located on external applicator 104. Optionally, applicator 104 is magnetically mounted directly to magnetically, attracted handle 102. In another variant, magnetically attracted back portion 110 comprises magnetically attracting material 118 and is connected to the rear of external applicator 104. In the event that magnetically attracting material 118 is added to resilient material 108, resilient material 108 is directly and removably, magnetically connected to magnetically attracted handle 102 and/or magnetically attracted back portion 110.

Magnetically attracting material 118 is constructed from a flexible strip material formed from non-metallic binding material with magnetic material embedded therein available from Bunting Magnetic Co., Elkgrove Village, Ill. in one embodiment. A type of flexible strip material available from Bunting Magnetic Co. is Type W which as equal magnetic holding strength on both sides of the material. Alternately, a suitable powdered metallic material such as iron oxide, can be mixed with rubber while it is in liquid form. In a conventional manner, this metallic material can be magnetized subsequent to the molding of the material. Magnetically attracting material 116 comprises a NITRILE Rubber Binder having embedded therein strips or rows of magnetic particles in one embodiment. This material is commercially available from 3M Corporation. Magnetically attracting material 116 are multi-pole magnets in one embodiment. Multi-pole magnets may have 2, 4, 6, etc. poles per inch. Magnetically attracting material 118 are standard magnets in yet a further embodiment. Magnetic segments for material 118 are commercially available from Magnetic Specialty, Inc., 707 Gilman Street, Marina, Ohio or Arnold Engineering Company, 614 Edmonds Lane, Suite #206, LewisviLle, Tex. 75067. The process of manufacturing flexible magnetic materials involves mixing, baking, pouring and injection molding the material in flat sheets. The flat sheets are then cut to a desired length, and then magnetized.

It is appreciated that the ergonomically friendly tool storage device of the present invention includes optional magnetically attracting material 118 disposed beneath barrier material 112, or as described above is included in the resilient material.

While only a few, preferred embodiments of the invention have been described hereinabove, those of ordinary skill in the art will recognize that the embodiment may be modified and altered without departing from the central spirit and scope of the invention. Thus, the preferred embodiment described hereinabove is to be considered in all respects as illustrative and not restrictive, the scope of the invention being indicated by the appended claims, rather than by the foregoing description, and all changes which come within the meaning and range of equivalency of the claims are intended to be embraced herein.

I claim:

1. An ergonomically friendly back lotion applicator for applying a lotion, cream or oil to a portion of a back of a user, said portion not readily accessible without the use of said lotion applicator, comprising:

a substantially rigid handle sized and dimensioned to allow said user to access said back; and, a substantially planar external applicator comprising a natural, porous, hide of an animal wrapped around a resilient material, said hide capable of temporarily retaining and transferring said lotion, cream or oil from said hide to said back of said user, said hide and said resilient material sized and dimensioned to automatically conform to at least a portion of said back upon application of pressure on said external applicator, and said external applicator removably connected to said handle.

2. The ergonomically friendly back lotion applicator of claim 1 in which said natural, porous, hide of an animal is selected from the group consisting of a mammal hide.

3. The ergonomically friendly back lotion application of claim 2 in which said mammal hide is selected from the group consisting of a deer hide, a cow hide, a lamb hide, and suede.

4. The ergonomically friendly back lotion applicator of claim 1 in which said external applicator includes a cream, lotion or oil barrier material disposed between said hide and said resilient material, whereby said barrier material prevents said resilient material from absorbing said cream, lotion or oil.

5. The ergonomically friendly back lotion applicator of claim 1 in which said external applicator is sized and dimensioned to be substantially congruent to a musco-skeletal portion of said back.

6. The ergonomically friendly back lotion applicator of claim 1 further comprising an external applicator side support, said side support being substantially rigid, and said hide and said resilient material rising vertically above said side support.

7. The ergonomically friendly back lotion applicator of claim 1 in which said resilient material is non-porous.

8. The ergonomically friendly back lotion applicator of claim 1 in which said resilient material comprises a liquid filled bladder.

9. The ergonomically friendly back lotion applicator of claim 1 in which said resilient material comprises a gel.

10. The ergonomically friendly back lotion applicator of claim 1 in which said resilient material comprises a curable compound.

11. The ergonomically friendly back lotion applicator of claim 1 in which said resilient material comprises a cured polyurethane.

12. The ergonomically friendly back lotion applicator of claim 1 in which said external applicator is removably magnetically mounted to said handle.

13. A kit for making a customized, ergonically friendly back lotion applicator, comprising at least one substantially rigid, handle sized and dimensioned to allow said user to access said back;

a plurality of differently sized and dimensioned external applicators, each said external applicator comprising a natural, porous, hide of an animal wrapped around a resilient material, said hide capable of temporarily retaining and transferring lotion, cream or oil from said hide to said back of said user, said hide and said resilient material sized and dimensioned to automatically conform to at least a portion of said back upon application of pressure said external applicator, said external applicator removably connected to said handle, and said external applicators having varying surface areas.

14. The kit of claim 13 in which said natural, porous, hide of an animal is selected from the group consisting of a mammal hide.

15. The kit of claim 14 in which said mammal hide is selected from the group consisting of a deer hide, a cow hide, a lamb hide, and suede.

16. The kit of claim 13 in which each said external applicator includes a cream, lotion or oil barrier material disposed between said hide and said resilient material, whereby said barrier material prevents said resilient material from absorbing said cream, lotion or oil.

17. The kit of claim 13 in which each said external applicator is sized and dimensioned to be substantially congruent to a different musco-skeletal portion of said back, whereby said user is capable of applying lotion to selected portions of said back.

18. The kit of claim 13 further comprising an external applicator side support, said side support being substantially rigid, and said hide and said resilient material rising vertically above said side support.

19. The kit of claim 13 in which said resilient material is non-porous.

20. The kit of claim 13 in which said resilient material comprises a liquid filled bladder.

21. An ergonomically friendly method of applying a lotion, cream or oil to a portion of a back of a user comprising:

providing an external applicator comprising a natural, porous, hide of an animal wrapped around a resilient material; connecting said external applicator to a handle of a length to allow said user to access all portions of said user's back; temporarily retaining said lotion, cream or oil on said hide; and, transferring said lotion, cream or oil from said hide to said back of said user.

22. The method of claim 21 in which said natural, porous, hide of an animal is selected from the group consisting of a manual hide.

23. The ergonomically friendly back lotion application of claim 22 in which said mammal hide is selected from the group consisting of a deer hide, a cow hide, a lamb hide, and suede.

* * * * *